(12) United States Patent
Thompson-Staples

(10) Patent No.: US 8,455,006 B1
(45) Date of Patent: Jun. 4, 2013

(54) ORGANIC HAIR CARE COMPOSITION AND METHODS OF MANUFACTURING AND USE

(76) Inventor: Anika Lee Thompson-Staples, Philadelphia, PA (US)

( * ) Notice: Subject to any disclaimer, the term of this patent is extended or adjusted under 35 U.S.C. 154(b) by 0 days.

(21) Appl. No.: 12/940,005

(22) Filed: Nov. 4, 2010

Related U.S. Application Data

(60) Provisional application No. 61/257,972, filed on Nov. 4, 2009.

(51) Int. Cl.
*A61K 35/64* (2006.01)
*A61K 36/63* (2006.01)

(52) U.S. Cl.
USPC ........... 424/539; 424/736; 424/744; 424/764; 424/70.2; 514/458

(58) Field of Classification Search
None
See application file for complete search history.

(56) References Cited

U.S. PATENT DOCUMENTS 6,723,309 B1 * 4/2004 Deane .......................... 424/70.1
2009/0130220 A1 * 5/2009 Johnson ........................ 424/539

OTHER PUBLICATIONS http://www.mountainroseherbs.com/learn/emulsifying_wax.php—accessed Feb. 2011.*
http://www.merriam-webster.com/dictionary/organic—accessed Feb. 2011.*

* cited by examiner

*Primary Examiner* — Susan Hoffman
(74) *Attorney, Agent, or Firm* — Leslie A. Thompson & Associates; Leslie A. Thompson

(57) ABSTRACT

An organic hair care composition made from organic ingredients, such as vegetable emulsifying wax, olive oil, shea butter, jojoba oil, and beeswax. The organic ingredients are mixingly introduced in predetermined proportions necessary to effectuate the styling, straightening, and therapeutic revitalization of hair in accordance with the included methods of manufacturing and use.

2 Claims, 3 Drawing Sheets

ORGANIC HAIR CARE COMPOSITION AND METHODS OF MANUFACTURING AND USE

REFERENCE TO RELATED APPLICATION

This application claims priority to U.S. Provisional Application No. 61/257,972 filed on Nov. 4, 2009, the entire content of which is incorporated herein by reference.

FIELD OF THE INVENTION

This invention relates to hair straightening and particularly to an organic hair care composition comprising vegetable emulsifying wax, olive oil, shea butter, jojoba oil, beeswax, vegetable glycerin, aloe vera, Vitamin E, emu oil, and assorted fragrances in proportions necessary to effectuate the styling and straightening of hair according to the preferred method of preparation and application of the invention. The invention also includes a method of manufacturing and use.

BACKGROUND OF INVENTION

The direct application of chemical compositions and heat to hair is a standard practice for straightening, curling, and generally styling hair into a myriad of hairstyles. This is typically accomplished using relaxers/hair straightening products containing harmful alkali metal hydroxides in conjunction with hair irons and pressing combs that are heated by electronic means or by the transfer of heat to the components that engage the hair. The use of strong chemical reagents and harmful alkali metal hydroxides usually serves to permanently straighten hair while often damaging the hair and the scalp in the process.

SUMMARY OF THE INVENTION

The invention relates to hair straightening and more particularly to a hair care composition that includes natural and organic ingredients and a method of manufacturing and using the same. The conventional methods of using heated irons or chemical relaxers and reagents to straighten hair are certainly less than ideal and tend to wreak havoc on healthy hair and scalps as a result of the harsh of sects of heat and chemicals over time or when improperly applied.

Accordingly an object of the present invention is to straighten hair naturally without the use of chemical relaxers or excessive heat or pressing combs that damage the hair and scalp.

Still another object of the present invention is to soften hair cuticles and allow effortless transition between hair textures via the reduction in the density of the cuticle without compromising the body, shine, or original texture of the hair.

A further object of the invention is to effectuate temporary straightening solutions that allow the texture of the hair to revert to a natural curl pattern from shampooing.

The end users of the present invention are a diverse lot. They can be individuals looking to transition between a natural curl pattern and a silky smooth straight finish. The organic hair care composition is ideal for someone who is transitioning out of the use of relaxers. Women experiencing menopause can use the organic hair care composition to keep their hair soft without the drying and breaking of hair caused by sweating. Men and women can universally employ the organic hair care composition without respect to gender for homogenous results. Individuals who wish to style their own hair can do so without many of the risks incumbent with chemical relaxers and, reagents as no damage can be caused by the ingestion or application of the organic hair care composition. The organic hair care composition is ideal for stylists who seek a better and healthier option for managing natural hair textures. Even a barber who wishes to relax a client's hair prior to cutting or shaping will find the organic hair care composition beneficial for this purpose. The organic hair care composition can be used on children with sensitive scalps to avoid the tangling and forceful pulling of their hair during the drying stage, thereby lessening or eliminating discomfort for a child to the delight of parents.

DETAILED DESCRIPTION

As a result of experimentation, the use of certain organic ingredients in predetermined proportions has been shown to effectively straighten hair while therapeutically restoring hair that has been over processed with heat and/or harsh chemicals. The major components of the subject hair straightening composition are vegetable emulsifying wax, olive oil, and shea butter processed in a solution with distilled water. Jojoba oil, beeswax, vegetable glycerin, and aloe vera are introduced into the aforementioned solution along with smaller amounts of Vitamin E, emu oil, and assorted organic fragrances like chamomile to enhance the olfactory appeal of the invention. The addition of shea butter; emu oil, and aloe vera liquid serve to condition the relaxed hair and add luster. The fragrances serve to obviate any unpleasant smells resulting from the mixture of the other ingredients.

The organic hair care composition primarily constitutes organic components and does not include any inorganic reagents that are chemical or harsh in nature. As a result, the organic hair care composition will foster maintenance of normal hair color and mitigate the effects of aging and over processing on bait while facilitating the growth of hair. The organic hair care composition of the present invention is oil-based and a plurality of oils is used to form a liquid base for the subsequent introduction of key ingredients. In one embodiment, the oils used ate organic oils that include, but are not limited to, natural vegetable oils. The preferred oils are olive oil and jojoba oil.

The olive oil represents the largest amount of oil and comprises at least nine (9) times the amount of jojoba oil in the preferred embodiment. This respective difference in the amount of oils can reasonably vary without impacting the effects of the invention. However, when olive oil and jojoba oil are included in the ingredients, the optimal blend will comprise at least 60% by weight of olive oil. The following is an example of the composition and ranges in Table 1.

TABLE 1

| INGREDIENT | AMOUNT |
|---|---|
| Vegetable emulsifying wax | 11-15 cups |
| Olive oil | 16-20 cups |
| Shea butter | 23-29 oz. |
| Jojoba oil | 1-3 cups |
| Beeswax | 8-11 oz. |
| Vegetable glycerin | ¼-½ cup |

TABLE 1-continued

| INGREDIENT | AMOUNT |
| --- | --- |
| Distilled water | 2.5-4.5 gal |
| Aloe vera liquid | 1-3 oz. |
| Vitamin E | <1 oz. |
| Emu oil | <1 oz. |
| Patchouli | <0.5 oz. |
| Chamomile | <0.5 oz. |
| Lemon oil | <0.5 oz. |

The amounts in Table I can vary without departing from the scope of the invention. In addition, other organic ingredients can be substituted for the ingredients listed above without departing from the scope of the invention.

Figure 1A:
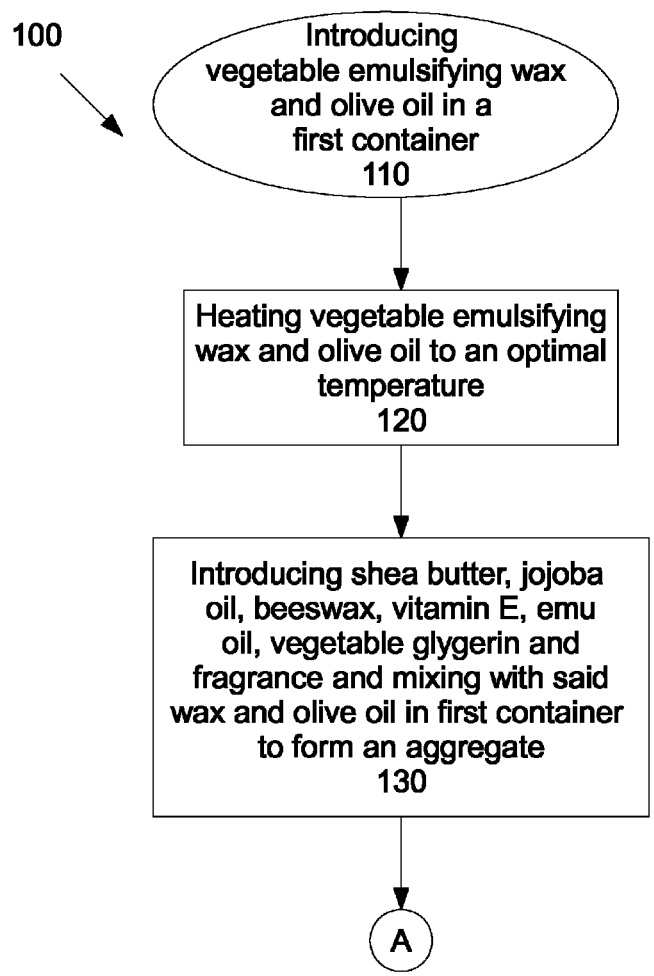
FIGS. 1A and 1B illustrate flow charts describing one embodiment of a method manufacturing an organic hair care composition to straighten hair.
Figure 1B:
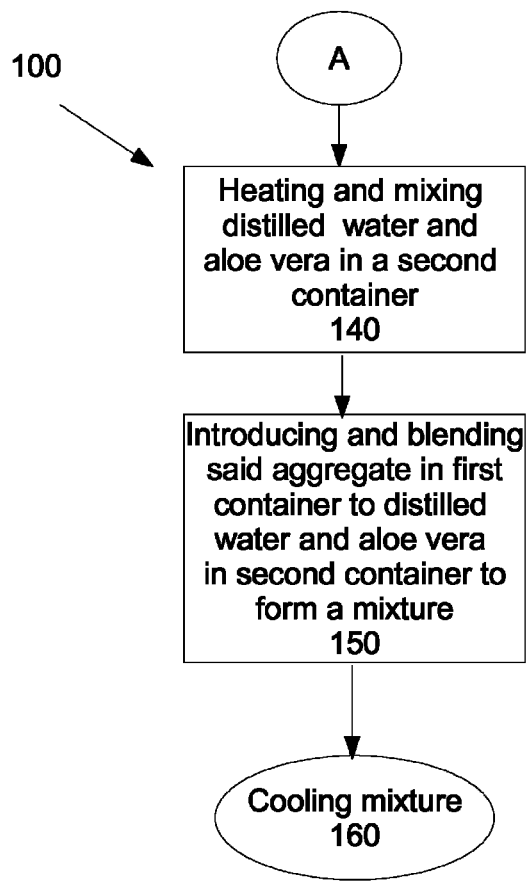
Figure 2:
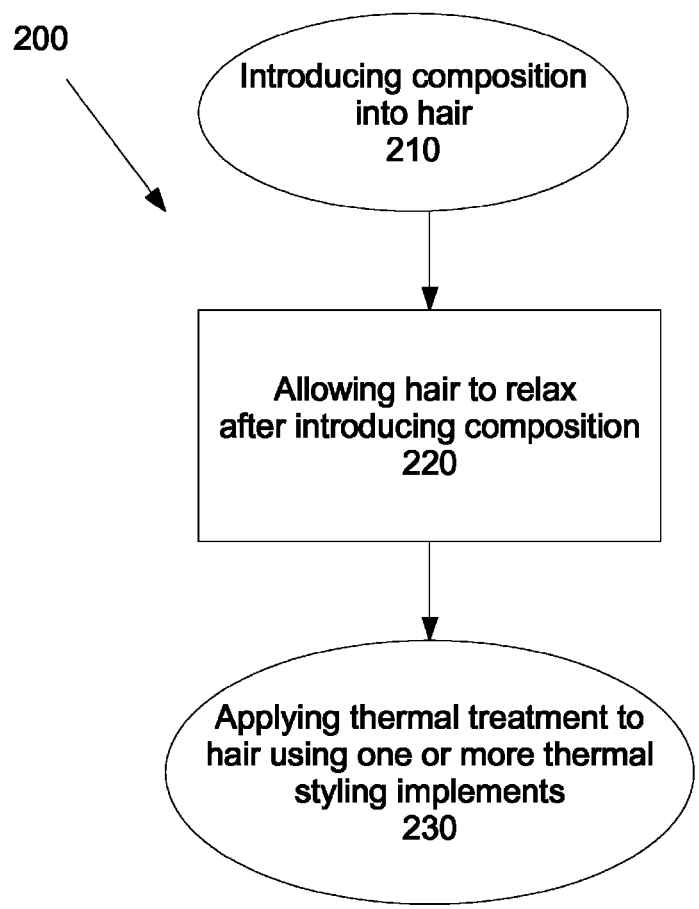
FIG. 2 illustrates a flow chart describing one embodiment of a method of using an organic hair care composition to straighten hair.

The present invention also teaches a method of manufacturing 100 the organic hair care composition, as outlined in FIGS. 1A and 1B. A first step includes introducing the vegetable emulsifying wax (or organic gel base) and olive oil in a first container 110 and heating the vegetable emulsifying wax and olive oil to an optimal temperature 120. The temperature of the olive oil is increased to thermally facilitate the dissolving of the olive oil in the wax base or gel base. Once the vegetable emulsifying wax and olive oil reach an optimal temperature, the rhea butter, jojoba oil, beeswax, Vitamin E, emu oil, vegetable glycerin and fragrances previously described are introduced into the first container 130 and heated and mixed until an aggregate is formed 130 but is completely melted and void of clumped matter. In a second container, the distilled water (preferably at room temperature) and aloe vera are heated and mixed therein 140. Subsequently, the heated aggregate from the first container is introduced into the second container to form a mixture 150. The entire contents of the second container are violently blended—preferably with an industrial strength mixer or the like—for at least thirty (30) minutes. The duration of this mixing step is dictated by the length of time required for the mixture to cool and solidify into a thick cream composition that is void of clumped matter. Once the resulting thick cream composition is cooled to room temperature 160, the thick cream composition can be placed in smaller containers to facilitate packaging for subsequent transport and distribution to end users. The respective steps for preparing the organic hair composition of the present invention can be adapted or modified to accommodate small scale to large scale production without departing from the scope of the invention.

The present invention also teaches a method of using the organic hair care composition to hair for subsequent straightening 200 with minimal or no damage. A user introduces an amount of the organic hair care composition into his or her hair 210. This step can be repeated as necessary to pervasively apply the organic hair care composition to the hair that will be straightened. The hair is then allowed to relax after introducing the composition 220 at this point without any chemical agents that are harmful to the hair. Once the organic hair care composition is sufficiently applied, the hair is ready for thermal treatment 230. The user or stylist can use Marcel irons, flat irons, pressing combs, and other thermal styling implements not expressly mentioned to apply direct heat to the coated hair for a myriad of styling options. In addition, the coated hair can be combed in conjunction with a blow dryer applying heated air, thereby effectuating a temporary straightening of the hair into a smooth, shiny, and bouncy finish. A user or stylist can vary the amounts of the organic hair care composition based on the result desired. The straightness of the hair is a function of how much organic hair care composition is applied. The respective steps for applying the organic hair composition of the present invention can be adapted or modified to accommodate different textures of hair without departing from the scope of the invention.

The organic hair care composition of the present invention is the result of extensive research and testing on human hair and human subjects. This research and testing supports the conclusion the organic hair care composition of the present invention effectively straightens hair with a silky smooth finish without the negative side effects of prior art products that include chemical reagents. Moreover, the organic hair care composition of the present invention softens hair cuticles and allows effortless transition between hair textures via the reduction in the density of the cuticle without compromising body, shine, or original texture of the hair.

While the present invention has been explained by a detailed description of a preferred embodiment, it is understood that various modifications and substitutions can be made with respect to the preferred embodiment or embodiment described herein within the scope of the present invention and its equivalents. It will be apparent, however, that variations and modifications may be made by those skilled in the art to the disclosed embodiments of the invention, with the attainment of some or all of its advantages and without departing from the spirit and scope of the present invention.

The invention claimed is:

1. A hair straightening composition consisting essentially of a range of 11 to 15 cups of vegetable emulsifying wax, a range of 16 to 20 cups of olive oil, a range of 23 to 29 ounces of shea butter, a range of 1 to 3 cups of jojoba oil, a range of 8 to 11 ounces of beeswax, a range of ¼ to ½ cup of vegetable glycerin, a range of 2.5 to 4.5 gallons of distilled water, a range of 1 to 3 ounces of aloe vera liquid, less than 1 ounce of vitamin E, less than 1 ounce of emu oil, less than 0.5 ounce of patchouli, less than 0.5 ounce of chamomile and less than 0.5 ounce of lemon oil.

2. The composition according to claim 1, wherein said composition therapeutically restores said hair that has been damaged by excessive heat or chemical hair treatments.

\* \* \* \* \*